(12) United States Patent
Eriksson

(10) Patent No.: US 6,888,631 B2
(45) Date of Patent: May 3, 2005

(54) MONITORING PARTICLES IN A FLUID FLOW

(75) Inventor: Klas Goran Eriksson, Asker (NO)

(73) Assignee: ABB Offshore Systems Limited (GB)

( * ) Notice: Subject to any disclaimer, the term of this patent is extended or adjusted under 35 U.S.C. 154(b) by 175 days.

(21) Appl. No.: 10/059,578

(22) Filed: Jan. 29, 2002

(65) Prior Publication Data
US 2002/0105645 A1 Aug. 8, 2002

(30) Foreign Application Priority Data
Feb. 5, 2001 (GB) .............................................. 0102825

(51) Int. Cl.⁷ .......................... G01N 15/02; G01N 21/00
(52) U.S. Cl. ........................ 356/335; 356/336; 356/338
(58) Field of Search ................................ 356/335, 336, 356/337, 338, 342, 441, 442

(56) References Cited

U.S. PATENT DOCUMENTS

| 3,714,444 A | * | 1/1973 | Carr et al. ................... 250/574 |
| 4,627,727 A | | 12/1986 | Jennings et al. |
| 4,647,780 A | | 3/1987 | Dunkel |
| 5,760,911 A | * | 6/1998 | Santschi et al. ............ 356/442 |

FOREIGN PATENT DOCUMENTS

| DE | 299 20 014 U1 | 10/2000 |
| EP | 0 337 108 A2 | 3/1989 |
| EP | 0 337 108 A | * 3/1989 |
| EP | 0 599 297 A1 | 11/1993 |
| EP | 1 061 356 A2 | 6/2000 |
| GB | 2097529 | 3/1982 |

OTHER PUBLICATIONS

Article: "ViPA—The Visual Process Analyser, Oil & Solids in Water," Jorin Limited; undated.
Article: "On–line determination of particle size and concentration (solids and oil) using ViPA Analyser," Jorin Limited; May 23, 2000.

* cited by examiner

Primary Examiner—Frank G. Font
Assistant Examiner—Roy M. Punnoose
(74) Attorney, Agent, or Firm—Howard B. Rockman; Barnes & Thornburg LLP

(57) ABSTRACT

Apparatus for use in monitoring particles in a fluid flow comprises: a duct (1) for receiving the fluid flow; light generating means (6) adjacent the duct for transmitting light into the fluid flow via a first at least partially light-transmissive part (4) of the duct; light-responsive detection means (7) adjacent a second at least partially light-transmissive part (5) of the duct for receiving light from the light generating means which has passed through the fluid flow; processing means (8) for location remotely from said duct; and means (9) for coupling the processing means with the detection means, the processing means being adapted for processing signals therefrom to provide data relating to particles in the fluid flow.

24 Claims, 1 Drawing Sheet

MONITORING PARTICLES IN A FLUID FLOW

CROSS REFERENCE TO RELATED APPLICATIONS

This application claims priority to United Kingdom application no. 010282517 filed on Feb. 5, 2003 to the extent permitted by law.

The present invention relates to monitoring particles in a fluid flow.

BACKGROUND OF THE INVENTION (1.) Field of the Invention

In oil production, a by-product is often water. This is commonly disposed of by injecting it under pressure into a well. While injecting this water, a matter of concern is its quality. Among the parameters of interest are the amount of dispersed oil and the amount of solid particles in the water. These parameters affect the injectivity of the water into the well. Particles with sizes down to a few micrometres have been shown to have a negative influence on the injectivity.

(2.) Description of the Related Art

An existing device for monitoring oil particles in water is disclosed in International Patent Application Publication No. WO 00/46586 and is embodied in an analyser called ViPA developed by Jorin Limited, 4 Vulcan Close, Sandhurst, Berkshire, United Kingdom—see also the paper "On-line determination of particle size and concentration (solids and oil) using ViPA Analyser", Dr Kami Nezhati, et al, presented at the "$7^{th}$ Annual International Forum Production Separation Systems", 23 May 2000, Oslo. However, such an analyser uses a special measurement cell, requiring a side-stream in the overall process. Also, the analyser is not directly suitable for subsea operation.

BRIEF DESCRIPTION OF THE SEVERAL VIEWS OF THE DRAWINGS

According to the present invention, there is provided apparatus for use in monitoring particles in a fluid flow, comprising:

a duct for receiving the fluid flow;

Figure 1:
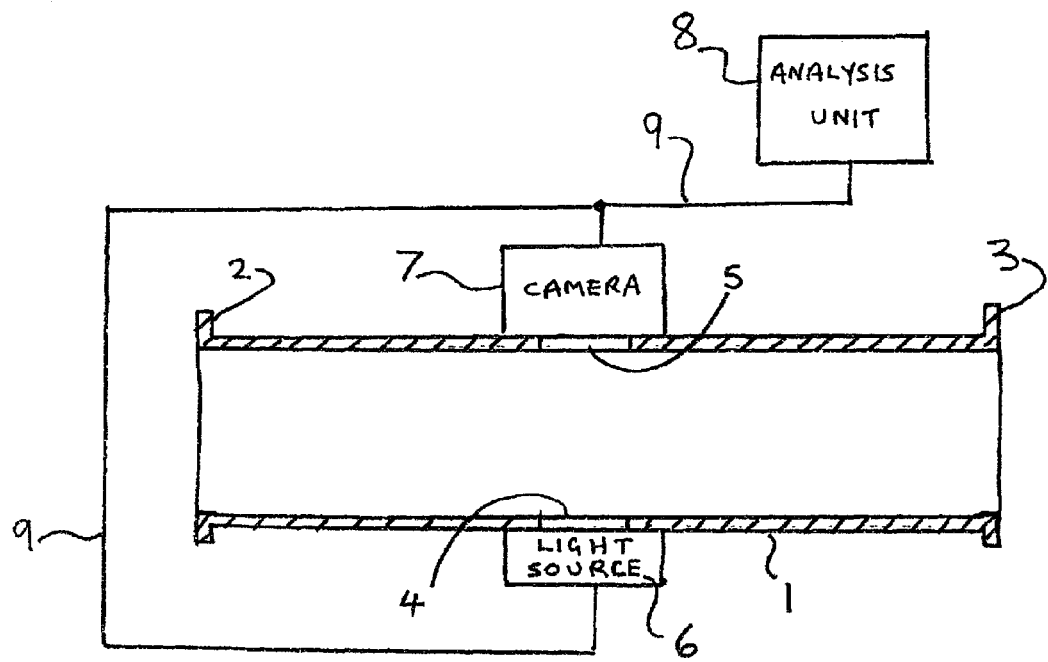

light generating means adjacent the duct for transmitting light into the fluid flow via a first at least partially light-transmissive part of the duct;

light-responsive detection means adjacent a second at least partially light-transmissive part of the duct for receiving light from the light generating means which has passed through the fluid flow;

processing means for location remotely from said duct; and means for coupling the processing means with the detection means, the processing means being adapted for processing signals therefrom to provide data relating to particles in the fluid flow.

Said duct may comprise a pipe section provided with means for mounting it in a run of pipework.

Said first and second at least partially light-transmissive parts may comprise first and second windows in a wall of the duct.

Said first and second at least partially light-transmissive parts may be diametrically opposite each other.

Inside said duct, each of said first and second at least partially light-transmissive parts may have a non-stick coating.

Said duct may be provided with means for flushing away deposits from each of said first and second at least partially light-transmissive parts inside the duct. Such flushing means may be located downstream of said first and second at least partially light-transmissive parts. The flushing means may comprise, for each of said first and second at least partially light-transmissive parts, a respective nozzle for directing a flushing fluid at the respective part from inside the duct.

Said light generating means may comprise a light-emissive diode, for example a plurality of such diodes, connected for example in parallel.

Said light-responsive detection means may comprise a television camera, for example being provided with a lens and frame grabbing means for capturing one magnified single image at a time, focussed inside said duct, the signals received by said processing means representing successive captured images from said grabbing means.

Said processing means may provide data relating to the amount and/or size distribution of particles of a predetermined kind in the fluid flow.

The surface of said first at least partially light-transmissive part inside said duct may be uneven for reducing deposit build-up on it.

The apparatus may include a plurality of such light-responsive detection means, and in this case it may be such that only one of said light-responsive detection means is used at a time. Also, each of said light-responsive detection means could be such that it receives light from said second at least partially light-transmissive part.

There may be a plurality of such first at least partially light-transmissive parts. In this case, there may be a plurality of such second at least partially light-transmissive parts, each of which is associated with a respective one of said first at least partially light-transmissive parts. In this case, where there is a plurality of light-responsive detection means, each of them may receive light from a respective one of such second at least partially light-transmissive parts.

The or each first and second at least partially light-transmissive parts may be associated with respective such flushing means.

There may be a plurality of such light generating means. In this case, the apparatus may be such that only one of said light generating means is used at a time. Where there is a plurality of first at least partially light-transmissive parts, each of said light generating means may be associated with a respective one of the first at least partially light-transmissive parts.

The invention also comprises an apparatus according to the invention in which said duct is mounted in pipework for conveying the fluid flow, the processing means being located at a location remote therefrom and the coupling means coupling the processing means and the light-responsive detection means. Said pipework may be for conveying water into a well in a hydrocarbon production system and in this case the first and second light-transmissive parts, the light generating means and the light-responsive means may be the sub-sea, said remote location being, for example, a topside platform.

The present invention also comprises a method of monitoring particles in a fluid flow, using apparatus according to the invention.

Figure 2:
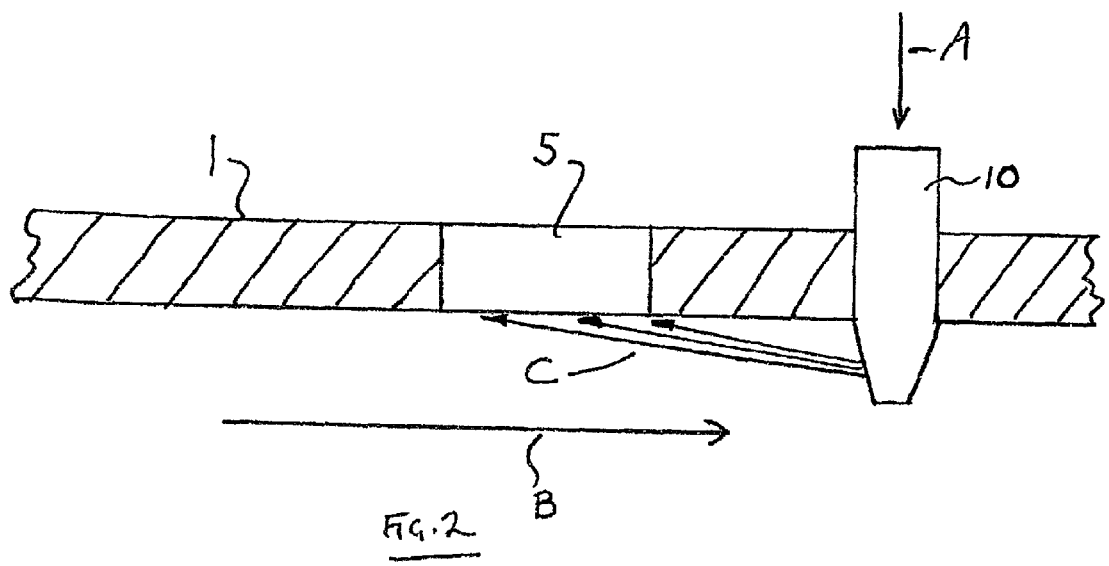

The present invention will now be described, by way of example, with reference to the accompanying drawings, in which:

FIG. 1 is a schematic view of an example of apparatus according to the invention; and FIG. 2 is a detailed view showing how flushing means may be provided.

DETAILED DESCRIPTION OF THE INVENTION

Referring first to FIG. 1, apparatus for use in monitoring particles, e.g. oil particles, in water being injected under pressure into a well in an oil production system comprises: a duct provided by a pipe section 1 having flanges 2 and 3 at opposite ends for mounting it in a run of pipework conveying such water; two diametrically opposite windows 4 and 5 in the wall of the pipe section 1; a light source 6 mounted at the window 4 for transmitting light into the pipe section 1; light-responsive detection means in the form of a picture capturing unit 7 mounted at the window 5; processing means in the form of an analysis unit 8 mounted at a location remote from the section of pipe 1, e.g. at a topside platform; and a power and communication link 9 which, on the one hand, provides power for the light source 6 and the picture capturing unit 7 and, on the other hand, provides for a communication channel coupling the picture capturing unit 7 with the analysis unit 8 to provide the latter with signals from the picture capturing unit 7.

The pipe section 1, the light source 6, and the picture capturing unit 7 are designed for sub-sea installation, while the analysis unit 8 is designed for a normal office environment. It may be a standard personal computer, with necessary communications facilities and software.

Light source 6 sends light through the window 4 into the pipe section 1. The light source 6 can, for example, use light emitting diodes. For redundancy and power increase, several light emitting diodes connected in parallel may be used. For optional further redundancy, several such groups can be used, with one switched on a time. Each such group could be associated with a respective such window 4.

The window 4 used at the light source 6 can optionally be given an uneven surface, taking into use the so called "Lotus effect". This effect is found in nature on the leaves of the lotus flower, and is exploited commercially in several products. The idea is basically that the uneven surface gives less contact area for any particle to attach to, such that the attracting forces between surface and particle are concentrated in a smaller area. This minimises the attractive force between particle and surface, and thus both minimises deposits forming, and makes flushing of deposits easier.

The picture capturing unit 7 outside the window 5 comprises a miniature television camera equipped with a microscope lens. The miniature camera captures a magnified picture with a focus slightly inside the window 5.

As the lifetime of the camera may be a concern, as an option a multitude of cameras can be used, which are turned on one by one as others cease to work. This multitude of cameras can either share the same window 5, or have separate such windows (each of which could be associated with a respective window 4 in the case where there are several such windows).

For each camera, a so-called "frame grabber" freezes one picture from the television camera at a time. Each frozen picture is then transmitted via the link 9 to the analysis unit 8.

If the pipe section 1 is mounted on the seabed, the analysis can then be mounted on a topside platform in a dry environment.

When one picture has been transmitted to the analysis unit 8, a second picture is taken and transmitted. After a sufficient number of pictures has been analysed (in the order of a few hundred), the analysis unit 8 has built up a good statistical count of the particles present. The analysis unit 8 can see the difference between a dispersed oil droplet and a solid particle from the shape. Thus, the amount of solid particles and dispersed oil droplets is independently determined.

The analysis unit 8 may process the information from the picture capturing unit 7 as disclosed in WO 00/46586 for example or as in the above-mentioned ViPA analyser of Jorin Limited.

The pipe section 1 could be, for example, about 51 cm (about 20 inches) long and have an internal diameter of about 15 cm (about 6 inches). The windows 4 and 5 can be made of diamond or sapphire, and a suitable non-stick coating can be applied to minimise build-up of, for example, wax deposits.

The molecules that can cause build-up are mainly wax and asphaltene molecules. Each window surface is thus tailored to minimise adhesion to such molecules. This will minimise deposits, but possibly not eliminate them completely.

In case deposits occur anyway, a secondary method of removing them is required. This may be done by high pressure methanol spraying. In sub-sea installations, high-pressure methanol is routinely available (as it is commonly used for avoiding hydrate formation during shutdown of oil streams).

In FIG. 2, is shown a methanol nozzle 10, which is used for intermittently flushing away deposits from the window using high pressure methanol injected into the nozzle in the direction of arrow A. The nozzle 10 is mounted downstream of the window 5 (arrow B indicating the direction of flow in pipe section 1) and directs the high pressure spray of methanol to the window 5 as shown by arrow C. There is a further such nozzle, mounted downstream from window 4. In the case where there is a multiplicity of cameras each with its own window, then each such window would be provided with its respective such nozzle.

The above described apparatus, using analysis unit 8, is capable of measuring simultaneously the amount of dispersed oil droplets and dissolved particles, with a resolution down to a few micrometres. Also, data may be provided relating to the amount of solid particles and oil droplets in the fluid flow and/or data relating to size distribution for solid particles and/or oil droplets in the fluid flow. Although the apparatus is primarily intended for sub-sea installation it could also be used elsewhere and the invention itself is not limited to use in a sub-sea installation.

What is claimed is:

1. Apparatus for use in monitoring particles in a liquid flow, comprising: a duct in the form of a pipe section for receiving the liquid flow;

light generating means adjacent the pipe section for transmitting light into the liquid flow via a first at least partially light-transmissive part of the pipe section;

light-responsive detection means adjacent a second at least partially light-transmissive part of the pipe section for receiving light from the light generating means which light has passed through the liquid flow;

processing means for location remotely from said pipe section;

means for coupling the processing means with the detection means, the processing means being adapted for processing signals therefrom to provide data relating to particles in the liquid flow;

wherein inside said pipe section, each of said first and second at least partially light-transmissive parts has a non-stick coating;

the surface of said first at least partially light-transmissive part inside said pipe section is uneven for reducing deposit build-up on said surface.

2. Apparatus according to claim 1, wherein said pipe section is provided with means for mounting said pipe section in a run of pipework.

3. Apparatus according to claim 1, wherein said first and second at least partially light-transmissive parts comprise first and second windows in a wall of the pipe section.

4. Apparatus according to claim 1, wherein said first and second at least partially light-transmissive parts are diametrically opposite each other.

5. Apparatus according to claim 1, wherein said flushing means is located downstream of said first and second at least partially light-transmissive parts.

6. Apparatus according to claim 1, wherein said flushing means comprises, for each of said first and second at least partially light-transmissive parts, a respective nozzle for directing a flushing liquid at the respective part from inside the pipe section.

7. Apparatus according to claim 1, wherein said camera is provided with a lens and frame grabbing means for capturing one magnified single image at a time, said lens and frame grabbing means focussed inside said pipe section, the signals received by said processing means representing successive captured images from said grabbing means.

8. Apparatus according to claim 1, wherein said processing means provides data relating to the amount and/or size distribution of particles of a predetermined kind in the liquid flow.

9. Apparatus according to claim 1, including a plurality of light-responsive detection means.

10. Apparatus according to claim 9, wherein only one of said light-responsive detection means is used at a time.

11. Apparatus according to claim 9, wherein each of said light-responsive detection means receives light from said second at least partially light-transmissive part.

12. Apparatus according to claim 1, including a plurality of first at least partially light-transmissive parts.

13. Apparatus according to claim 12, including a plurality of second at least partially light-transmissive parts, each of which is associated with a respective one of said first at least partially light-transmissive parts.

14. Apparatus according to claim 13, including a plurality of light-responsive detection means, wherein each of said light-responsive detection means receives light from a respective one of said second at least partially light-transmissive parts.

15. Apparatus according to claim 12, wherein said pipe section is provided with means for flushing away deposits from each of said first and second at least partially light-transmissive parts inside the pipe section and wherein each of said first and second at least partially light-transmissive parts is associated with respective flushing means.

16. Apparatus according to claim 1, wherein there is a plurality of light generating means.

17. Apparatus according to claim 16, wherein only one of said light generating means is used at a time.

18. Apparatus according to claim 16, including a plurality of such first at least partially light-transmissive parts and wherein each of said light generating means is associated with a respective one of said first at least partially light-transmissive parts.

19. Apparatus according to claim 1, with said pipe section mounted in pipework for conveying the liquid flow, the processing means being located at a location remote therefrom and the coupling means coupling the processing means and the light-responsive detection means.

20. Apparatus according to claim 19, wherein said pipework is adapted to convey water into a well in a hydrocarbon production system.

21. Apparatus according to claim 20, wherein said pipe section, the first and second light-transmissive parts, the light generating means and the light-responsive means are sub-sea.

22. Apparatus according to claim 21, wherein said remote location is a topside platform.

23. Apparatus according to claim 1 wherein said pipe section is provided with means for flushing away deposits from each of said first and second at least partially light-transmissive parts inside the pipe section.

24. Apparatus according to claim 1 wherein said light-responsive detection means comprises a television camera.

* * * * *